US00PP19462P3

(12) United States Plant Patent
Jensen

(10) Patent No.: US PP19,462 P3
(45) Date of Patent: Nov. 18, 2008

(54) ***CAMPANULA* PLANT NAMED 'PKMF02'**

(50) Latin Name: *Campanula formanekiana*
Varietal Denomination: PKMF02

(75) Inventor: Gert Kim Jensen, Odense (DK)

(73) Assignee: Gartneriet PKM A/S, Odense N (CK)

( * ) Notice: Subject to any disclaimer, the term of this patent is extended or adjusted under 35 U.S.C. 154(b) by 0 days.

(21) Appl. No.: 11/713,745

(22) Filed: Mar. 5, 2007

(65) Prior Publication Data

US 2008/0222762 P1 Sep. 11, 2008

(51) Int. Cl.
*A01H 5/00* (2006.01)

(52) U.S. Cl. ..... Plt./414

(58) Field of Classification Search ..... Plt./414

See application file for complete search history.

(56) References Cited

PUBLICATIONS

Print–out of application No. and filing date from European Union–Community Plant Variety Office (CPVO) website (www.cpvo.fr) for corresponding, international PBR application, CPVO 2007;0042 filed Jan. 3, 2007.
Print–out of application No. and filing date from Canadian Food Inspection Agency—Plant Breeder's Right Office (CPVO) website (www.inspection.gc.ca) for corresponding, Canadian PBR application No. 07–5888 filed Apr. 20, 2007.
Japanese Plant Breeder's Rights Application 20998 filed Apr. 25, 2007.

*Primary Examiner*—Kent L. Bell
*Assistant Examiner*—June Hwu
(74) *Attorney, Agent, or Firm*—Foley & Lardner LLP

(57) ABSTRACT

A new and distinct cultivar of *Campanula* plane named 'PKMF02', characterized by having upright, compact plant habit; dense and bushy plant form, mainly due to short, upright and stiff stems; vigorous growth habit, and with no need for chemical growth retardation; higher number of flowers per plant; large, upright, violet-blue flowers; more cutting on each stock plant; reduced need for cold treatment after flower induction; and shorter period for forcing the flowers after the cold treatment.

3 Drawing Sheets

Latin name of genus and species of the plant claimed: *Campanula formanekiana.*
Variety denomination: 'PKMF02'.

BACKGROUND OF THE INVENTION

The present invention relates to a new and distinct cultivar of *Campanula* plant, botanically known as *Campanula formanekiana,* commonly known as Bellflower, and hereinafter referred to by the name 'PKMF02'.

The new *Campanula,* 'PKMF02', is a product of a planned breeding program conducted by the inventor, Gert K. Jensen, in Søhus, Denmark. The objective of the breeding program is to develop a new *Campanula* cultivar with uniform and compact plant form and violet-blue flowers.

The new *Campanula* cultivar originated from a cross made in a controlled breeding program by the inventor in 2000 in Søhus, Denmark. The female or seed parent is a *Campanula formanekiana* cultivar designated 'FORMET' (described in EU-CPVO patent EU 11437). The male or pollen parent is an unpatented *Campanula formanekiana* cultivar designated '11.02.0059B'. The new *Campanula* 'PKMF02' was discovered and selected by the inventor as a single flowering plant within the progeny of the stated cross in week May of 2002 in a controlled environment in Søhus, Denmark. The inventor selected 'PKMF02' on the basis of its high number of cuttings per stock plant, short vernalization period and short forcing time after vernalization. Plant of 'PKMF02' are more upright, compact and freely flowering than plants of the wild type.

Asexual reproduction of the new *Campanula* cultivar by terminal cuttings was first performed in February of 2004 in Søhus, Denmark, and has demonstrated that the combination of characteristics as herein disclosed for the new cultivar are firmly fixed and retained through successive generations of asexual reproduction.

SUMMARY OF THE INVENTION

The following traits have been repeatedly observed and are determined to be the unique characteristics of 'PKMF02'. These characteristics in combination distinguish 'PKMF02' as a new and distinct cultivar:

1. Upright, compact plant habit;
2. Dense and bushy plant form, mainly due to short, upright and stiff stems;
3. Vigorous growth habit, and with not need for chemical growth retardation;
4. Higher number of flowers per plant;
5. Large, upright, violet-blue flowers;
6. More cutting on each stock plant;
7. Reduced need for cold treatment after flower induction; and
8. Shorter period for forcing the flowers after the cold treatment.

Side-by-side comparisons were conducted by the inventor in Søhus, Denmark between 1) plants of the new *Campanula formanekiana* 'PKMF02' and the female or seed parent, *Campanula formanekiana* 'FORMET' (described in EU-CPVO patent EU 11437), and 2) plants of the new *Cam-*

*panula formanekiana* 'PKMF02' and the *Campanula formanekiana* wild type. Plants of 'PKMF02' differ in the following characteristics to both 'FORMET' and the wild type:

1. Plants of 'PKMF02' have large, violet-blue, upright, single and campanulate flowers;
2. Plants of 'PKMF02' have shorter internodes, petioles, and leaves;
3. Plants of 'PKMF02' have shorter peduncles;
4. Plants of 'PKMF02' are more compact in shape;
5. Plants of 'PKMF02' produce more flowers per plant;
6. Plants of 'PKMF02' produce more cutting on each stock plant;
7. Plants of 'PKMF02' have less need for cold treatment for flower induction; and
8. Plants of 'PKMF02' have a shorter period for forcing the flowers after cold treatment.

No plants of the male or pollen parent, the unpatented *Campanula formanekiana* cultivar designated '11.02.0059B', are available to conduct a side-by-side botanical comparison to plants of the new *Campanuala formanekiana* 'PKMF02'.

BRIEF DESCRIPTION OF THE PHOTOGRAPHS

The accompanying colored photographs illustrate the overall appearance of the new *Campanula* 'PKMF02', showing the colors as true as it is reasonably possible to obtain in colored reproductions of this type. Colors in the photographs may differ slightly from the color values cited in the detailed botanical description, which more accurately describe the actual colors of 'PKMF02'.

DETAILED BOTANICAL DESCRIPTION

Figure 1:
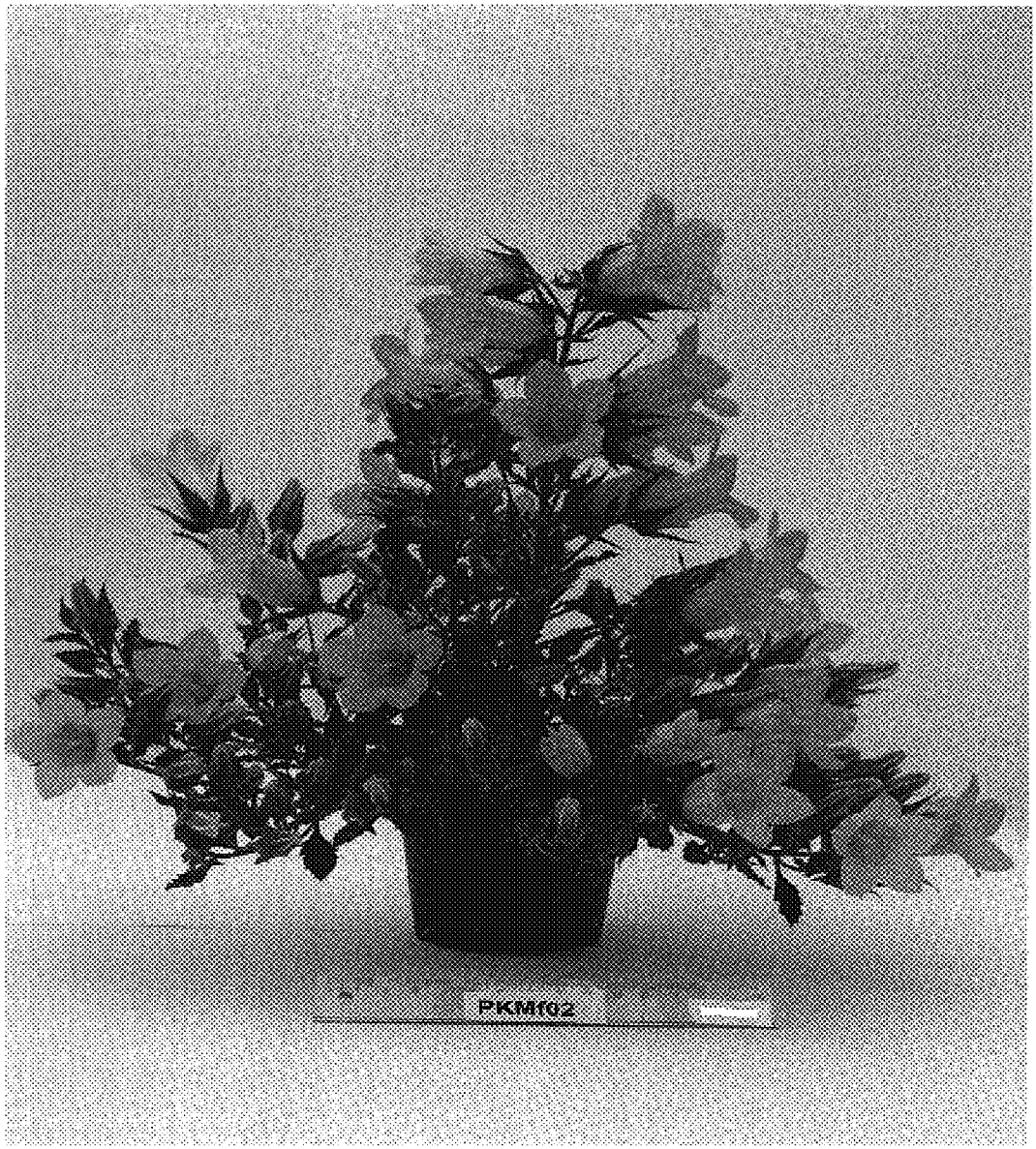
FIG. 1 shows a side perspective view of a typical flowering plant of 'PKMF02', as grown in a 10.5 cm pot at 14 weeks of age.
Figure 2:
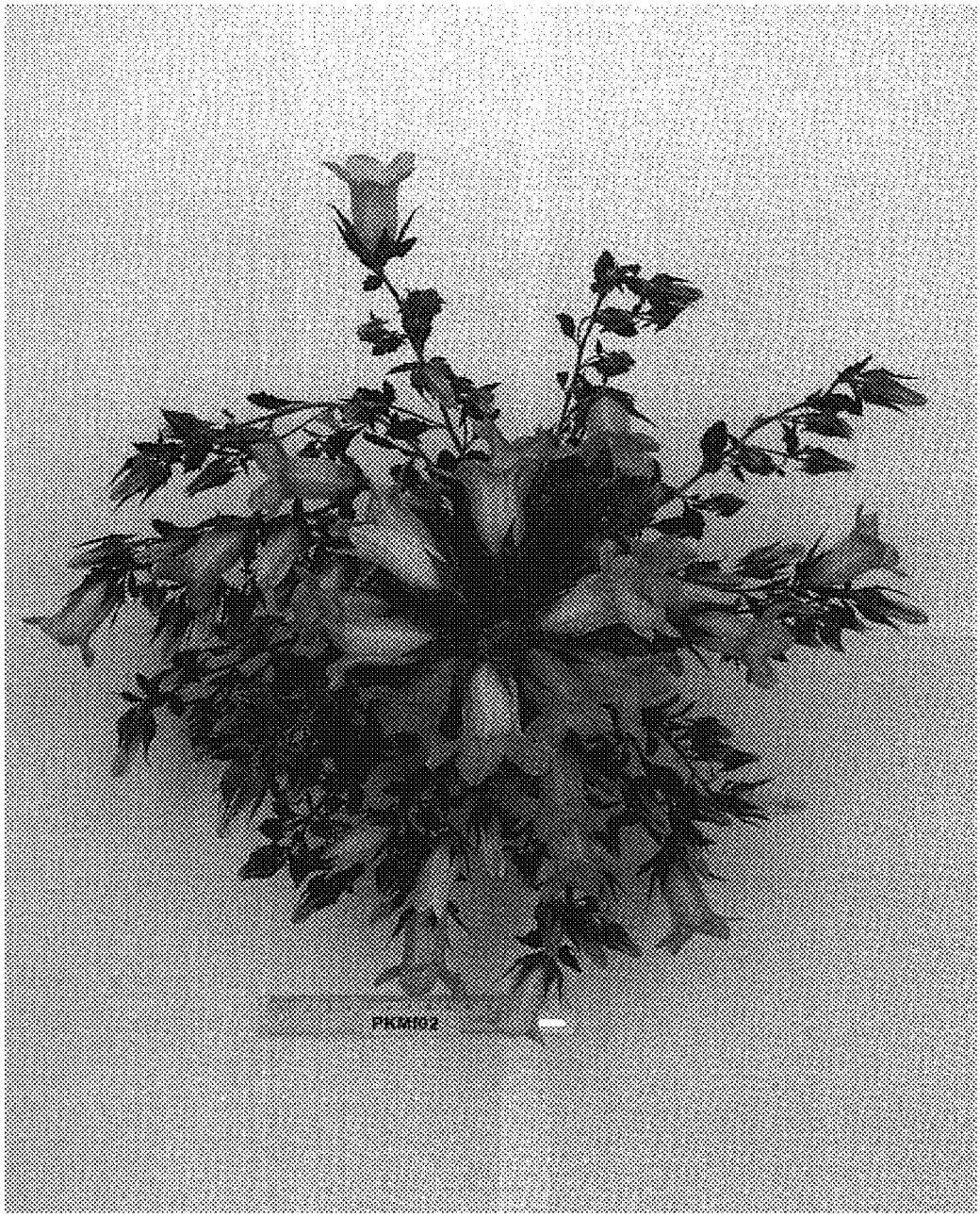
FIG. 2 shows a top perspective view of a typical flowering plant of 'PKMF02', as grown in a 10.5 cm pot at 14 weeks of age.
Figure 3:
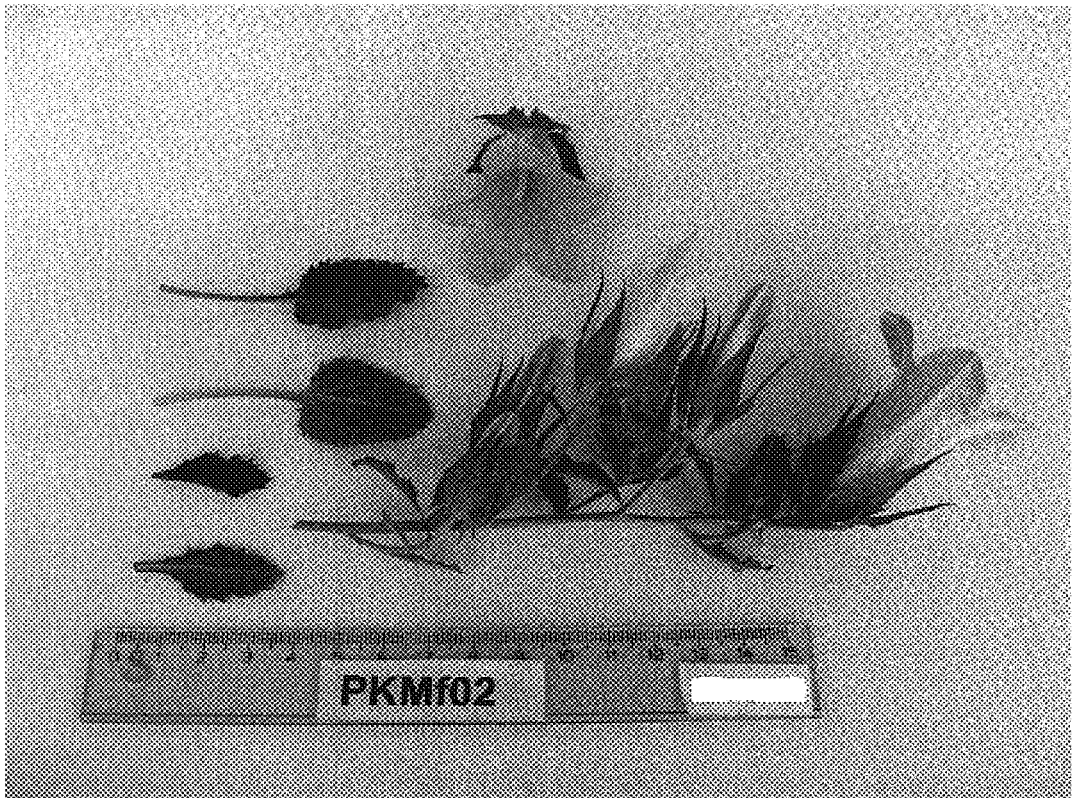
FIG. 3 show a close-up view of typical flowering raceme and leaves of 'PKMF02' at 14 weeks of age.

The new *Campanula* 'PKMF02' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMF02' as grown in a heated and lighted, glass-covered greenhouse in Søhus, Denmark, under conditions which closely approximate those generally used in commercial practice where day temperatures in the greenhouse range from 18–22° C. and the night temperature averages about 16° C. Ambient light levels used while growing plants of 'PKMF02' are +90Wm$^2$. Plants of 'PKMF02' are grown with 18 hour long day photoperiodic treatments from the third week and forced to flower after cold treatment at the same day length. Propagation and seedlings are exposed to 10 hour short photoperiodic treatments. No growth retardants used.

The age of the 'PKMF02' plants described is 14 weeks old and grown in 10.5 cm pots. The photographs and descriptions were taken during the winter season when day temperatures in glass-covered greenhouse range from 18–20° C. and when night average temperatures in glass-covered greenhouse range from 16–18° C.

Color references are made to The Royal Horticultural Society Colour Chart (R.H.S.), 4$^{th}$ edition, except where general colors of ordinary significance are used.

Classification:

*Botanical.*—*Campanula formanekiana.*

Parentage:

*Female or seed parent.*—*Campanula formanekiana* designated 'FORMET' (described in EU-CPVO patent EU 11437).

*Male or pollen parent.*—*Campanula formanekiana* designated '11.02.0059B' (unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Biennial rosette plant with irregular, globular plant habit. Campanulate flowers in racemes. Freely branching with lateral branches forming at every node; dense and bushy.

*Crop time.*—After rooting, about 18 weeks are required to produce finished flowering plants in 10.5 cm pots.

*Vigor.*—Vigorous growth rate.

*Plant height* (*from pot rim to top of plant plane*).—About 30 to 35 cm.

*Plant spread* (*width*).—About 50 cm.

*Lateral branches.*—Habit: Freely branching. Quantity: About 20–30 per plant. Leaves per Lateral Branch: About 10 to 15. Length (including flowers): 15 cm to 25 cm. Diameter: About 2 mm to 3 mm. Internode Length: 1.5 cm to 2.5 cm.

*Stem.*—Shape: Round. Strength: Strong. Aspect; Upright and outward. Pubescence: Short hairs, hispidolous. Color: RHS 138B, green.

Foliage description:

*Basal leaves.*—Arrangement: Single, rosulate. Overall shape: Ovate. Apex shape: Acute. Base shape: Attenuate. Length: About 20 mm to 60 mm. Width: About 15 mm to 20 mm. Margin: Serate to biserate. Texture (both sides): Pubescent. Pubescence: Very short, stiff hairs on both sides, hispidolous.

*Apical* (*stem*) *leaves.*—Arrangement: Single, alternate. Overall shape: Ovate to lanceolate, sessile. Length: About 20 mm to 60 mm. Width: About 10 mm to 20 mm. Margin: Serate to biserate. Texture (both sides): Pubescent. Pubescence: Very short, stiff hairs on both sides, hispidolous.

*Basal & apical leaves.*—Foliage Color: Mature: Upper surface: Green, RHS 133A. Lower surface: Green, RHS 137B. Immature: Upper surface: Green, RHS 137A. Lower Surface: Green, RHS 137B. Venation: Pattern: Reticulate. Color: Upper surface: Green, RHS 133A. Lower Surface: Green, RHS 138B. Petiole: Length: Basal Leaves: Sessile or about 5 mm to 60 mm. Apical (Stem) Leaves: Sessile or about 2 mm to 20 mm. Diameter: Basal Leaves: About 0 mm to 2 mm. Apical (Stem) Leaves: About 0 mm to 4 mm. Color: RHS 138B, green. Texture: Pubescent.

Inflorescence description:

*Flower arrangement and shape.*—Single, large, campanulate flowers in raceme turning upright to outward, basipetal flowering habit.

*Natural flowering season.*—June to July. Season can be extended by long day treatments.

*Time to flower.*—About 8 weeks after vernalization (cold treatment).

*Flower longevity.*—On the plant, flowers last about 5 to 9 days; however, longevity of individual flowers is highly dependent on temperature and light conditions. Flowers persistent.

*Fragrance.*—Sweet.

*Inflorescence size.*—Height: 15 cm to 35 cm. Diameter: 5 to 25 cm.

*Number of flowers per inflorescence.*—5 to 25.

*Number of flowers per lateral stem.* 5 to 10.

*Number of flowers and buds per plant.*—About 150 to 250.

*Buds.*—Length: Up to 45 mm. Diameter: Up to 12 mm. Shape: Oblong, petals, forming a ribbed tube. Color: RHS 157A to RHS 91C.

*Flowers.*—Height: About 50 to 55 mm. Diameter: About 50 mm. Petals: Arrangement: Single, sympetalous, basal fused campanulate. Quantity per flower: About 5. Length: Lobes about 15 mm; whole petal about 50 mm to 55 mm. Width: About 7 mm. Overall Shape: Lanceolate. Tip: Cuspidate. Base: Fused. Margin: Entire. Texture: Silky. Color (when opening): Upper and under surface, green-white, RHS 157A. Color (when opened): Upper and under surfaces, violet-blue, RHS 91B. Fading: No fading, but withers to violet-blue, RHS 91A.

*Sepals.*—Arrangement: Basally fused. Appearance: Upper surface: Pubescent, short, soft white hairs. Lower surface: Pubescent, short, soft white hairs. Quantity per flower: 5. Length: About 30 mm to 40 mm. Width: About 10 to 15 mm. Overall shape: Lanceolate. Tip: Acuminate. Base: Sagittate. Margin: Serate to biserate. Texture: Upper surface: Pubescent, short, soft white hairs. Lower surface: Pubescent, short, soft white hairs. Color (immature): Upper and under surfaces, green, RHS 138A. Color (mature): Upper and under surfaces: green, RHS 138A.

*Peduncles.*—Length: About 40 mm to 70 mm. Diameter: About 2–3 mm. Strength: Strong. Color: Green, RHS 138B. Texture: Pubescent, short, soft, white hairs.

*Pedicels.*—Angle: Acute. Length: About 4 to 7 mm. Diameter: About 1 to 2 mm. Strength: Strong. Color: Green, RHS 138B. Texture: Pubescent, short, soft, white hairs.

Reproductive organs:

*Androecium.*—Stamen: Quantity: 5. Anther: Shape: Lanceolate, antisepalous, introse, basifixed and two-celled. Twisting when withering. Length: About 12 mm (just before flowering opening). Color: Yellow, RHS 10C (Just before flowering opening) and yellow, RHS 11B (when withering). Pollen: Amount: Plenty. Color: Yellow, RHS 10B.

*Gynoecium.*—Pistil: Quantity: 1. Length: About 30 mm to 40 mm. Stigma: Shape: Tripartite. Color: Yellow-green, RHS 149C. Style: Length: About 20–25 mm. Color: White, RHS 155A. Ovary: Color: White, RHS 155A with yellow-orange, RHS 17C, nectary.

Seed/fruit: None observed.

Weather tolerance: Plants of the new *Campanula* have exhibited good tolerance to drought, rain and wind, with low temperature resistance to 0° C.

Disease/pest resistance: Not tested.

Disease/pest susceptibility: Not tested.

I claim:

1. A new and distinct cultivar of *Campanula* plant named 'PKMF02', as illustrated and described herein.

* * * * *